US00PP25090P3

(12) United States Plant Patent
Zaiger et al.

(10) Patent No.: US PP25,090 P3
(45) Date of Patent: Nov. 25, 2014

(54) INTERSPECIFIC TREE NAMED 'AUTUMN ZEE'

(50) Latin Name: ***Interspecific Prunus* species**
Varietal Denomination: Autumn Zee

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/986,288

(22) Filed: Apr. 19, 2013

(65) Prior Publication Data

US 2014/0317793 P1 Oct. 23, 2014

(51) Int. Cl.
*A01H 5/08* (2006.01)

(52) U.S. Cl.
USPC ..... Plt./180

(58) Field of Classification Search
CPC ..... A01H 5/00; A01H 5/0862; A01H 5/0843; A01H 5/0868
USPC ..... Plt./180
See application file for complete search history.

(56) References Cited

PUBLICATIONS

Federal Register vol. 75, No. 64, 2010 Rules and Regulation, 17027-17031.*

* cited by examiner

*Primary Examiner* — June Hwu
*Assistant Examiner* — Keith Robinson

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth habit.
2. Fruit with an attractive red skin color.
3. Fruit with good storage and shipping quality.
4. Fruit with good flavor and eating quality.
5. Fruit maturing very late in the season.

1 Drawing Sheet

Botanical designation: Interspecific *Prunus* species.
Variety denomination: 'Autumn Zee'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Candy Stripe' Interspecific (U.S. Plant Pat. No. 17,828), 'Flavorfall' Interspecific (U.S. Plant Pat. No. 11,990) and our non-patented proprietary interspecific seedlings with the field identification numbers '288LK54', '41EH357', '67Z80', '82EG355' and '324LF168'.

STATEMENT REGARDING FEDERALLY SPONSORED RESEARCH AND DEVELOPMENT

Not applicable.

ORIGIN OF THE VARIETY

The new and distinct interspecific tree consists of *Prunus salicina, Prunus armeniaca* and *Prunus persica*. It was originated by us in our experimental orchard located near Modesto, Calif. as a first generation cross between our proprietary non-patented interspecific seedlings with the field identification numbers '19HD447' and '31M208'. The seed parent (19HD447) interspecific (non-patented) originated from a cross of our non-patented proprietary interspecific seedling '288LK54' and 'Candy Stripe' Interspecific (U.S. Plant Pat. No. 17,828). The non-patented interspecific pollen parent (31M208) originated as an open pollinated seedling selection from our non-patented interspecific proprietary seedling '41EH357' which is a first generation cross from our non-patented interspecific proprietary seedling '67Z80' and 'Flavorfall' Interspecific (U.S. Plant Pat. No. 11,990). A large number of these first generation seedlings were budded onto older established trees of 'Nemaguard' Rootstock (non-patented) to enhance earlier fruit production. Under close and careful observation the present budded seedling exhibited desirable fruit and tree characteristics and was selected in 2007 for additional asexual propagation and commercialization.

ASEXUAL REPRODUCTION OF THE VARIETY

In 2007 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree [Plum× Apricot×Peach] which has vigorous, upright growth and is a regular and productive bearer of large fruit with an attractive red skin color. The fruit is further characterized by its firm flesh, good flavor and good storage and shipping quality. In comparison to its seed parent (19HD447) interspecific (non-patented) the fruit of the new variety has firmer flesh and is approximately 25 days later in maturity. In comparison to its pollen parent (31M208) interspecific (non-patented) the fruit of the new variety has brighter red skin color and is approximately 50 days later in maturity. In comparison to the commercial variety 'Flavorfall' Interspecific (U.S. Plant Pat. No. 11,990) (its ancestor) the fruit of the new variety is approximately 15 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies with type of soil, fertility and cultural practices.

*Form*.—Upright, usually pruned to vase shape.

*Branching habit*.—Upright, crotch angle approximately 35°, increases with heavy crop load.

*Productivity*.—Productive, sets 1.5 to several times the amount of fruit desired, thinning and spacing of fruit necessary for marketable size fruit. Varies with climatic conditions during bloom time.

*Bearer*.—Regular, good fruit set 5 consecutive years. No alternate bearing observed.

*Fertility*.—Self-sterile, pollinator required.

*Density*.—Medium dense, usually pruned to vase shape to increase amount of sunlight to center of tree to enhance fruit color, Brix and health of fruit wood.

*Hardiness*.—Hardy in all stone fruit growing areas of California. Tree grown in USDA Hardiness Zone 9. Winter chilling requirement is approximately 1000 hours at or below 45° F.

Trunk:

*Size*.—Large. Average circumference of 65.7 cm at 23 cm above ground on a 7 year old tree.

*Stocky*.—Medium stocky.

*Texture*.—Medium shaggy, roughness increases with age of tree.

*Color*.—Varies from 5Y 3/2 to 7.5Y 3/4.

Branches:

*Size*.—Medium. Average circumference 8.5 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 47 in a 25.8 square cm section of branch. Average length 3.6 mm. Average width 1.3 mm. Color varies from 2.5Y 5/6 to 5Y 5/6.

*Color*.—New growth varies from 5GY 6/6 to 5GY 5/6. Mature growth varies from 10YR 5/2 to 10YR 3/2, varies with age of growth.

Leaves:

*Size*.—Medium. Average length 96.6 Average width 45.9 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Small to medium. Average length 11.6 mm. Average width 1.6 mm. Longitudinally grooved. Surface glabrous. Color varies from 2.5GY 8/4 to 2.5GY 7/4.

*Glands*.—Type — globose. Number varies from 0 to 2, average number 2. Size — medium. Average length 1.3 mm. Average width 0.6 mm. Located primarily on the base of the leaf blade and upper portion of the petiole. Color varies from 2.5GY 7/6 to 5GY 7/6.

*Stipules*.—None present.

*Color*.—Upper surface varies from 5GY 4/6 to 7.5GY 4/4. Lower surface varies from 5GY 5/4 to 7.5GY 5/4. Midvein color varies from 2.5GY 7/4 to 5GY 7/4.

Flower buds:

*Size*.—Small to medium. Average length 9.6 mm. Average diameter 5.2 mm.

*Hardiness*.—Hardy with respect to California winters.

*Form*.—Conical, becoming elongated just before opening.

*Pedicel*.—Average length 5.0 mm. Average width 0.8 mm. Color varies from 5GY 6/8 to 5GY 5/8. Surface glabrous.

*Color*.—N 9.5/(white).

*Number of buds per spur*.—Varies from 6 to 13, average number 9. Varies with age of spur.

Flowers:

*Blooming period*.—Date of First Bloom Mar. 11, 2012. Date of Petal Fall Mar. 21, 2012, varies slightly with climatic conditions.

*Size*.—Small to medium. Average height 10.2 mm. Average diameter 16.6 mm.

*Petals*.—Normally 5, alternately arranged to sepals. Petal apex — rounded. Petal base — rounded to somewhat truncated. Size — small to medium. Average length 8.4 mm. Average width 7.7 mm. Form — obovate. Arrangement — sinuate. Color N 9.5/(white). Both upper and lower surfaces glabrous.

*Sepals*.—Normally 5, alternately arranged to petals. Size — small to medium. Average length 2.8 mm. Average width 2.5 mm. Shape — ovate. Apex rounded to triangular. Margin — entire. Both upper and lower surfaces glabrous. Color — upper surface varies from 5GY 7/10 to 5GY 6/8. Lower surface varies from 5GY 6/6 to 5GY 6/8.

*Stamens*.—Average number per flower 30. Average filament length 8.0 mm. On average, the stamens are below the height of the petals. Filament color N 9.5/(white). Anther color 2.5YR 5/10.

*Pollen*.—Self-sterile, pollinator required. Color varies from 5Y 7/8 to 5Y 7/10.

*Pistil*.—Number — normally 1. Average length 8.9 mm. Position of stigma an average of 0.9 mm below anthers. Surface glabrous. Color varies from 2.5GY 8/6 to 2.5GY 7/6.

*Fragrance*.—Heavy.

*Color*.—N 9.5/(white).

*Number flowers per flower bud*.—Average 2, varies from 1 to 4.

*Pedicel*.—Average length 5.2 mm. Average width 0.9 mm. Color varies from 5GY 6/8 to 5GY 5/8. Surface glabrous.

Fruit

*Maturity when described*.—Firm ripe and ready for consumption.

*Date of first picking*.—Oct. 26, 2012.

*Date of last picking*.—Nov. 2, 2012, varies slightly with climatic conditions.

*Size*.—Medium to large. Average diameter axially 62.7 mm. Average transversely in suture plane 63.4 mm. Average weight 152.5 grams, varies slightly with fertility of the soil, amount of thinning and climatic conditions.

*Form*.—Globose.

*Suture*.—Nearly smooth, extends from base to apex.

*Ventral surface*.—Nearly smooth.

*Apex*.—Nearly round.

*Base*.—Varies from flat to slightly retuse.

*Stem cavity*.—Rounded to slightly elongated in suture plane. Average depth 3.2 mm. Average diameter 4.9 mm.

Stem:

*Size*.—Small. Average length 8.9 mm. Average diameter 2.3 mm.

*Color*.—Varies from 7.5YR 4/6 to 7.5YR 3/4.

Flesh:

*Ripens*.—Evenly.

*Texture*.—Firm.

*Fibers*.—Few, small, tender.

*Firmness*.—Firm, having good handling and shipping quality.

*Aroma*.—Slight.

*Amydgalin*.—Undetected.

*Eating quality*.—Good.

*Flavor*.—Good, a good balance between acid and sugar.

*Juice*.—Moderate amount, enhances flavor.

*Acidity*.—Not available.

*Brix*.—Average Brix of 15.1°, varies slightly with amount of fruit per tree and climatic conditions.

*Color*.—Varies from 5Y 9/2 to 7.5Y 8.5/2.

*Pit cavity*.—Average length 27.0 mm. Average width 18.6 mm. Average depth 6.6 mm. Color varies from 10YR 6/8 to 2.5Y 7/4.

Skin:

*Thickness*.—Medium.

*Surface*.—Smooth to very slightly waffled.

*Bloom*.—Moderate amount, completely covered.

*Tendency to crack*.—Very slight.

*Color*.—Ground color varies from 2.5Y 8/8 to 2.5Y 8/10. Overspread with 7.5R 3/10 to 7.5R 2/6.

*Tenacity*.—Tenacious to flesh.

*Astringency*.—Undetected.

Stone:

*Type*.—Clingstone, medium adherence.

*Size*.—Medium. Average length 26.1 mm. Average width 17.4 mm. Average thickness 11.1 mm.

*Form*.—Ovoid.

*Base*.—Varies from flat to slightly pointed.

*Apex*.—Pointed. Average length 0.2 mm.

*Surface*.—Very slightly pitted throughout. One shallow groove on each side of suture extending from base to apex.

*Sides*.—Unequal, one side extending further outward from suture plane.

*Ridges*.—Very small and short extending from base towards apex.

*Tendency to split*.—None.

*Color*.—Varies from 7.5YR 4/6 to 10YR 6/6 when dry.

Kernel:

*Size*.—Small to medium. Average length 14.8 mm. Average width 8.0 mm. Average depth 8.2 mm.

*Form*.—Ovoid.

*Viability*.—Viable, complete embryo development.

*Skin color*.—Varies from 7.5YR 4/6 to 10YR 4/6.

Use: Dessert. Market — local and long distance.

Keeping quality: Good, held firm in cold storage at 38° to 42° F. for 3 weeks without internal breakdown of flesh or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

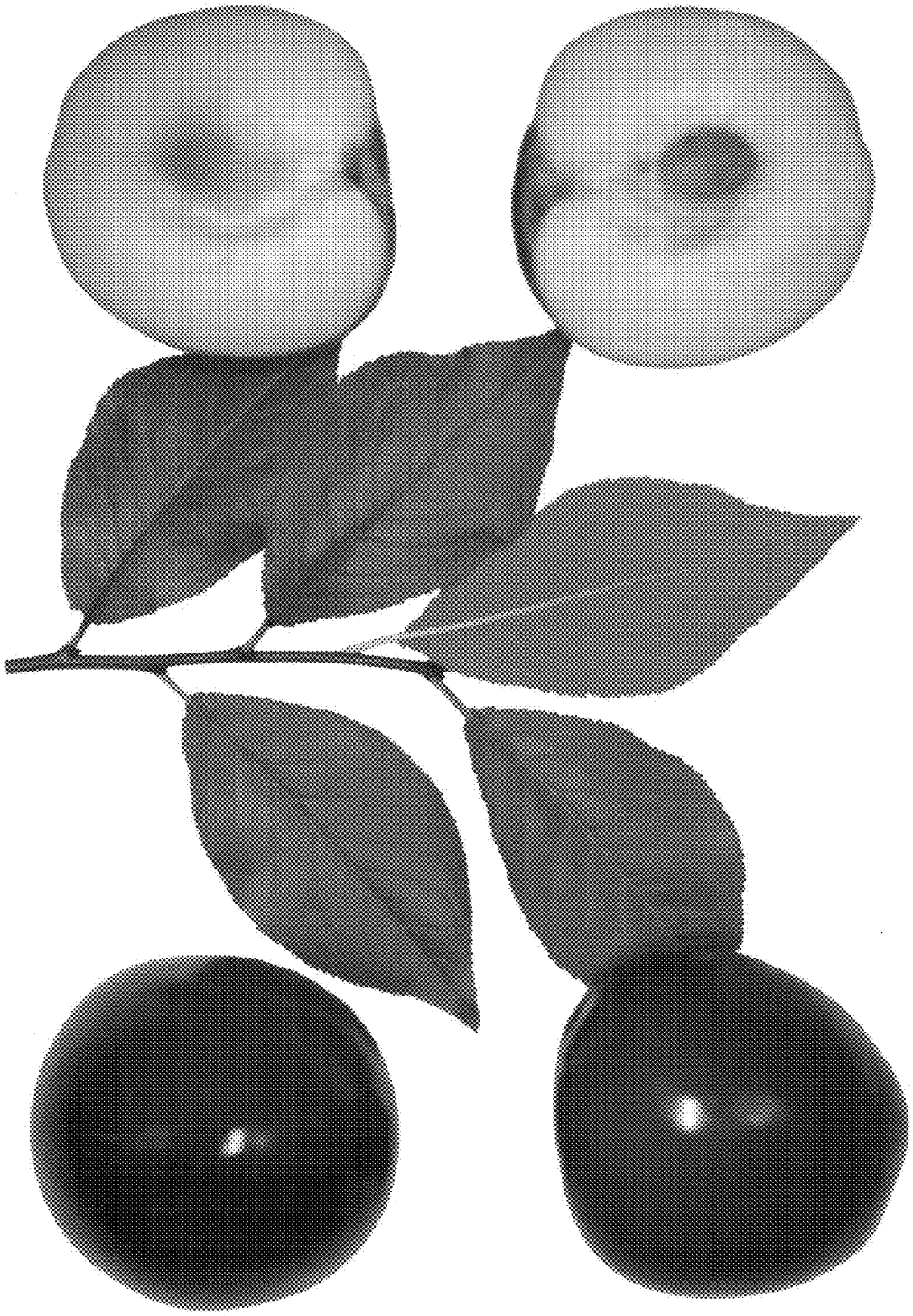

* * * * *